United States Patent [19]

Banko

[11] 3,945,375

[45] Mar. 23, 1976

[54] ROTATABLE SURGICAL INSTRUMENT

[75] Inventor: Anton Banko, Bronx, N.Y.

[73] Assignee: Surgical Design Corporation, Long Island, N.Y.

[22] Filed: Apr. 30, 1973

[21] Appl. No.: 355,914

Related U.S. Application Data

[63] Continuation-in-part of Ser. No. 241,019, April 4, 1972, Pat. No. 3,844,272, which is a continuation-in-part of Ser. No. 799,476, Feb. 14, 1969, Pat. No. 3,732,858, which is a continuation-in-part of Ser. No. 762,286, Sept. 16, 1968, Pat. No. 3,528,425.

[52] U.S. Cl. ............... 128/6; 128/276; 128/305
[51] Int. Cl.² A61B 1/06; A61M 1/00; A61B 17/32
[58] Field of Search ........... 83/672; 128/6, 11, 303, 128/303.15, 2 B, 304, 311; 241/62; 350/96 B; 27/24 A

[56] References Cited

UNITED STATES PATENTS

| | | | |
|---|---|---|---|
| 899,175 | 9/1908 | Meyer | 128/6 |
| 1,292,326 | 1/1919 | Jacobson | 128/11 UX |
| 1,493,240 | 5/1924 | Bohn | 128/305 |
| 1,663,761 | 3/1928 | Johnson | 128/305 |
| 2,341,388 | 2/1944 | Rocca | 27/24 A |
| 2,599,662 | 6/1952 | Rosenbaum | 128/6 |
| 2,674,777 | 4/1954 | Davis | 27/24 A |
| 2,699,770 | 1/1955 | Fourestier | 128/6 |
| 3,082,805 | 3/1963 | Royce | 128/2 B |
| 3,320,957 | 5/1967 | Sokolik | 128/311 |
| 3,496,931 | 2/1970 | Pilling | 128/6 |
| 3,614,953 | 10/1971 | Moss | 128/305 |
| 3,618,611 | 11/1971 | Urban | 128/305 |

OTHER PUBLICATIONS

"Spiral Point Trochar", advertisement of the Royal Rubber Co., Akron, Ohio. The Embalmer's Monthly, May, 1950, Back Cover Page. 027–024 A.

Primary Examiner—Channing L. Pace
Attorney, Agent, or Firm—Darby & Darby

[57] ABSTRACT

An instrument for removing tissue including a rotatable fluted cutter member housed in a probe adapted to be inserted into a portion of a body from which tissue is to be removed. The instrument can supply irrigation fluid through the probe to the area being operated upon and evacuate the material through the probe after being engaged by the cutter.

20 Claims, 13 Drawing Figures

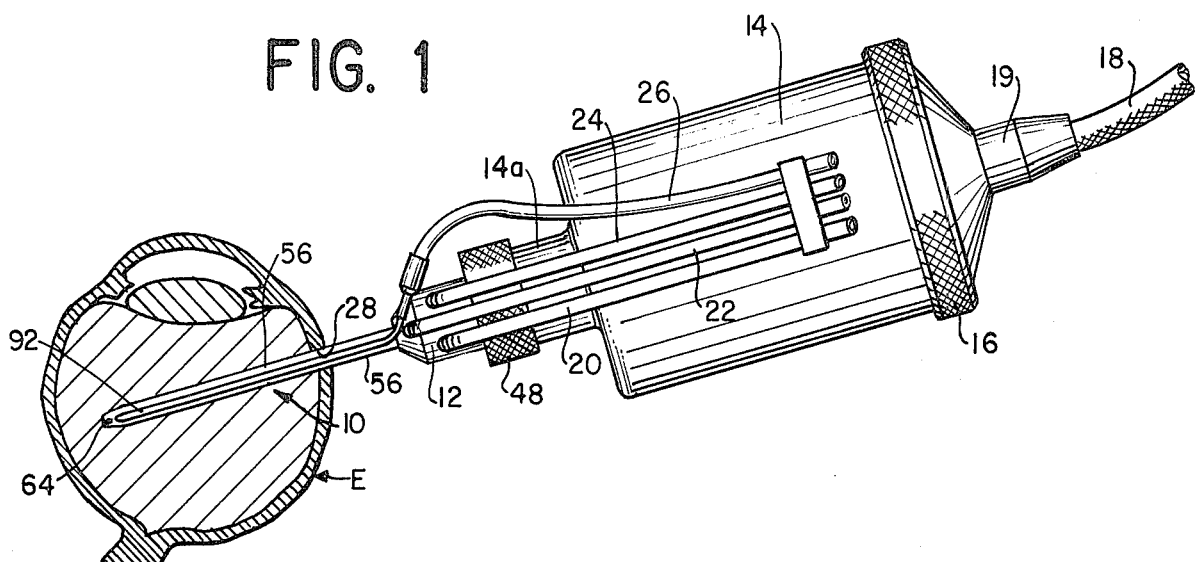
FIG. 1
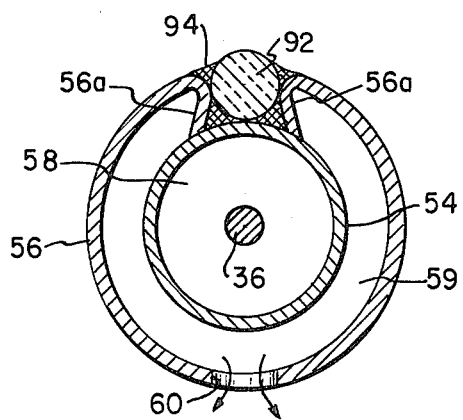
FIG. 9
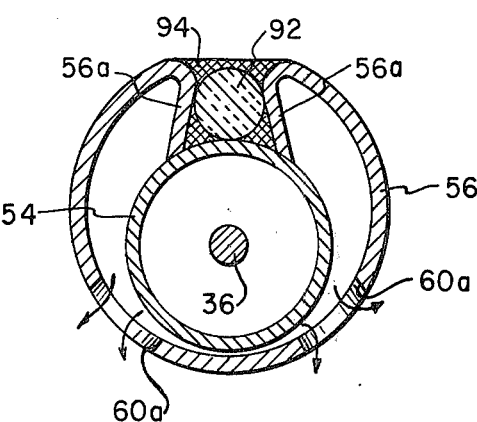
FIG. 10
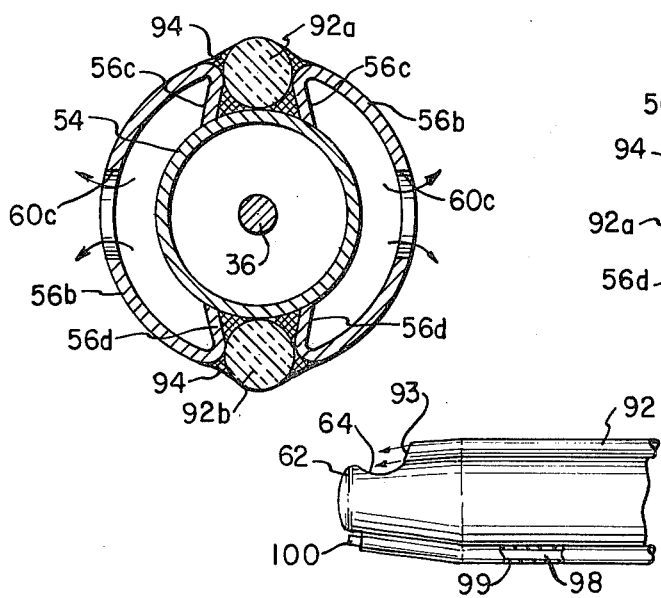
FIG. 11
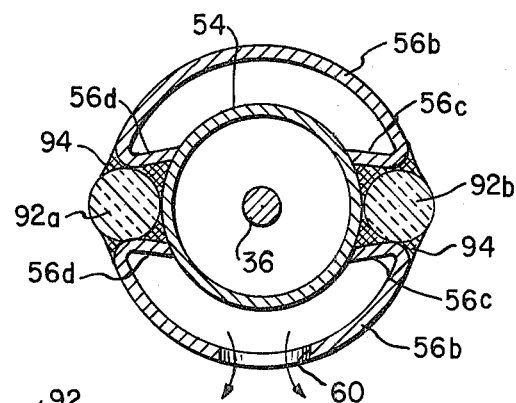
FIG. 12
FIG. 13

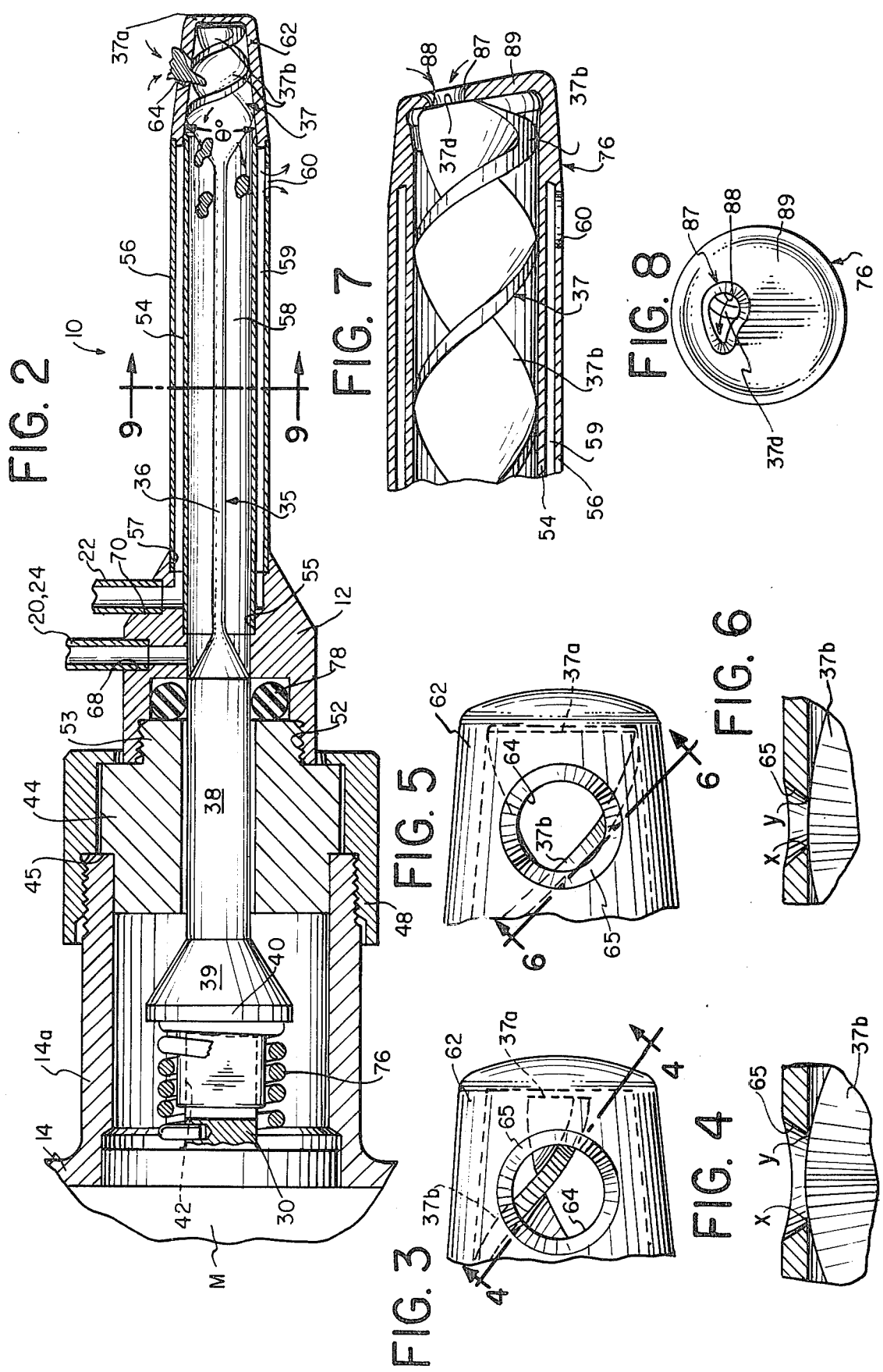

ROTATABLE SURGICAL INSTRUMENT

CROSS REFERENCE TO RELATED APPLICATIONS

This application is a continuation-in-part of my prior copending application Ser. No. 241,019, filed Apr. 4, 1972, now U.S. Pat. No. 3,844,272 dated Oct. 29, 1974 entitled "Surgical Instruments", that application being in turn a continuation-in-part of applicant's then copending application Ser. No. 799,476, filed Feb. 14, 1969, now U.S. Pat. No. 3,732,858, dated May 15, 1973, which in turn is a continuation-in-part of the then copending application Ser. No. 762,286, filed Sept. 16, 1968, now U.S. Pat. No. 3,528,425, dated Sept. 15, 1970. All of the said applications are assigned to the assignee of the subject application.

GENERAL DESCRIPTION

In the foregoing prior patent applications, various forms of instruments are disclosed and claimed which are adapted for holding, cutting, and removal of tissue from the body. The present invention also relates to instruments of the same general type and, more specifically, to improvements of one type of instrument disclosed in applicant's copending application Ser. No. 241,019. More specifically, the subject application is directed to an instrument adapted for cutting tissue, such as bands and membranes, from relatively inaccessible locations, such as the eye.

In accordance with the invention, a rotatable fluted drill type cutter is utilized. The cutter is rotated by a motor. The cutter is located at the end of a probe which includes an opening into which tissue or other substances enter. The instrument also supplies irrigation fluid through the probe to the field being operated upon. In addition, the instrument is capable of supporting additional instrumentation, such as cryogenic or electrical electrodes as well as fiber optics for illumination and/or viewing the operating field.

It is therefore an object of the present invention to provide an instrument for removing tissue from a portion of the body.

An additional object is to provide an instrument for removing material from the body in which a probe is to be inserted into the body, the instrument including a rotatable fluted cutter.

A further object is to provide an instrument for removing tissue from the body which can carry additional instrumentation, such as optical members and electrodes, to the operating site.

Yet another object is to provide an instrument for removing tissue from the body in which the instrument brings tissue into a cutting relationship with a rotatable cutter.

Other objects and advantages of the present invention will become more apparent upon reference to the following specifications and annexed drawings, in which:

FIG. 1 is an overall plan view of the instrument shown for use in performing an operation in the eye;

FIG. 2 is a cross-sectional view of a portion of the instrument showing the details thereof;

FIGS. 3–6 are fragmentary views, with FIGS. 4 and 6 being partially in cross-section, showing the operation of the cutter;

FIG. 7 is a fragmentary view of the end of the probe, showing the details of the cutter of another embodiment of the instrument;

FIG. 8 is a front view of the tip of the probe of the instrument of FIG. 7;

FIGS. 9–12 are views in cross-section of various forms of probes carrying auxiliary instrumentation; and FIG. 13 is a plan view, partly in cross-section, of a further embodiment of the invention.

Referring to FIG. 1, the instrument includes a probe 10 extending from a fluid supply cup 12 which in turn is attached to a motor housing 14. The housing 14 contains a cnventional electric motor (not shown) and is closed off by a cap 16 which is threaded and otherwise sealed to the main housing 14. Cables 18 extend through a grommet 19 in the cap 16 to supply current to the motor. A suitable switching circuit (not shown) for the motor can be provided at a location remote from the instrument.

Extending outside the housing, and attached to the housing if desired, are three fluid flow conduits 20, 22 and 24. These conduits respectively provide evacuation force, irrigation fluid and a reverse flow fluid through cup 12 to the probe 10 in a manner to be described. An optical rod, or bundle of optic fibers, 26 are also attached to the probe 10 for purposes to be described.

The probe 10 is shown in FIG. 1 inserted through an opening 28 in the eye E. The probe 10 has located therein a cutter (not shown in FIG. 1) which is adapted to cut tissue from within the eye. The cut tissue is removed via the evacuation conduit 20. It should be understood, of course, that the instrument can be used at any body location of a human or animal.

FIG. 2 shows the details of the instrument. The motor housing 14 contains the motor M which has an output shaft 30 extending into a neck 14a on the housing. The instrument has a cutting tool 35 which includes a shaft 36, a fluted drill type cutter 37, and a shank 38 whose end is fastened to a holder 39 having a shoulder 40. Holder 39 has a partial internal bore 42 which fits over the motor shaft 30.

The cutting tool shank 38 fits in a bushing 44 having a shoulder 45 which is held against the end of neck 14a by a collar 48 threaded onto housing neck 14a.

The fluid supply cup 12 is threaded at 52 onto a shoulder 53 on bushing 44. A pair of tubular shells 54 and 56 are mounted on internal steps 55 and 57 on the front end of the cup 12. Inner shell 54 defines a central flow passage for evacuation force and reverse fluid flow while the space between shells 54 and 56 defines a passage 59 for the flow of irrigation fluid. The irrigation fluid exits through an opening 60 located near the end of the outer shell 56.

The front ends of both shells 54 and 56 are sealed off by a nose cone 62 of truncated conical shape. The shells 54, 56 and the cone 62 are made of a suitable biologically inert metal material, such as stainless steel, so the cone can be welded to the shells. The nose cone 62 has an opening 64 at a selected position along its length. As shown in FIGS. 3–6, the opening 64 is of generally circular shape and has an inwardly tapering wall 65. The lower edge of wall 65 is sharpened to form a cutting edge. In the embodiment of FIGS. 1 and 2 opening 64 is preferably disposed 180° from the irrigation fluid opening 60.

Cup 12 is formed with a first stepped bore 68 into which the fluids from both conduits 20 and 24 is applied. It is preferred that the two conduits 20 and 24 be connected together by a suitable T fitting (not shown) external to probe 10 and a common outlet conduit inserted in bore 68. The outlet of the bore 68 communicates with the probe's interior passage 58 of the probe so that the passage can receive both suction and reverse flow-fluids. Similarly, cup 12 is formed with a second bore 70 to accept and hold the irrigation fluid conduit 22. The bore 70 communicates with the passage 59 between shells 54 and 56 and the fluid exits out the outlet opening 60.

The evacuation force for conduit 20 is produced by any suitable means. A constant displacement type pump can be used to produce the evacuation. The irrigation fluid for conduit 22 and the reverse flow fluid for conduit 24 are preferably sterile solutions, for example, saline solutions of the same or different salinity.

The cutter 37 of cutting tool 35 is urged against the inner surface of the front end of the nose cone 62 by a spring 76 which acts between the end of the motor 14 and the shoulder 40 of key 39. Thus, a force is always exerted forwardly and longitudinally of the axis of tool 35. An O-ring 78 is placed over shank 38 in cup 12 between a shoulder of the cup terminating the passage through which the cutter extends and the bushing neck 53. This seals off fluid between bore 68 and the motor housing 14, and the atmosphere.

The cutter tool shaft 36 between the shank 38 and the drill 37 is preferably of a material which has some degree of flexibility or elasticity. For example, it has been found that stainless steel is a satisfactory material having a dimension, for example, of 0.022 inch. The flexibility of shaft 36 and the use of spring 76 urges the drill 37 into engagement with the inner surface of cone 62 at all times.

The cutter 37 can also be formed of the same, or similar material as the shaft 36. If desired, the complete cutting tool 35 can be milled or otherwise suitably formed of a single piece of material.

The cutter 37 has one or more flutes each having a cutting edge. When rotating, the flutes form a generally barrel-like body. The front end 37a is spaced from the inside surface of the front end of the cone 62.

The cutter 37 can be formed with one or more flutes 37b with sharp edges which rotate around and advance along the body of the cutter like the sprial of a screw thread. The principal requirement of the flute or flutes is that they extend in front of and in back of the opening 64 during a complete cycle of rotation of tool 35 so that there always will be engagement of the cutting surface of the flutes 37b with the cutting surface of the wall 65 surrounding the opening 64.

It has been found that the nose cone 62 should have a taper of substantially about 5½° on each side of the center line forming a total included angle of approximately 11°. If the angle is made substantially smaller than this, the end result will be that the cutter 37 will tend to seize on the interior of the nose cone. If the angle is larger than this, then the outer diameter of the nose cone and the probe will have to be increased substantially and, also, it becomes more difficult to make an effective engagement of the cutting surfaces of cutter 37 with the opening 64. A large axial force will be required by the spring 76 to produce the same adhering force between the rotating edge of cutter 37 and the stationary edge of wall 65.

The cutter 37 has two points of support against the inner wall of the nose cone before a cutting edge of a flute sweeps across opening 64. One will be adjacent the opening and the other will be on the opposite of that particular flute. As seen in FIGS. 3–6, when a cutting edge sweeps across the opening it has three points of support. Two, $x$ and $y$ in FIG. 3–6 are with the stationary cutting edge of wall 65 and the other is on the opposite side of the particular flute with the inner surface of the nose cone. The chord through points $x$ and $y$ has the same inclination as the inner surface of the nose cone and coincides with that surface. That is, the cutting edge extends into the opening. The flexible shaft 36 permits the cutter to align its position to achieve the three points of support.

The operation of the instrument proceeds as follows. An incision is first made in the portion of the body into which the probe is inserted. The probe is then inserted through the body opening. The motor 14 can be operated to energize the cutter tool 35 to cause the blades, or flutes of cutter drill 37 to rotate with respect to the shearing edges 65 of the opening 64.

Evacuation is applied through conduit 20 and the central passage to draw tissue into the opening 64. As the cutter 37 rotates, as shown in FIGS. 4–6, the flutes sweep across the opening 64. The outer diameter of flute of cutter 37 and the inner diameter of the nose cone are such that the flute's cutting edge extends into the opening 64. The spring 76 urges the tool 35 forward. The tissue caught between the edge of the cutter blade and the wall 65 of the opening 64 is carried along with the rotation of the flute until there is a shearing cut made between the blade and the wall. In this way, tissue is cut each time a cutting edge of the flute passes under the opening 64 during each rotation of the tool 35.

The particles of tissue cut off and any fluid removed from the operating field are moved down the central passage 58 out through the conduit 20 into a collecting receptacle (not shown).

Irrigating fluid can be supplied from the conduit 22 through the outer passage 59 and out the opening 60. This can be done at the same time the tissue is being cut and removed from the operating field. The irrigating fluid can serve several functions. First of all, it can be supplied to an enclosed operating field, such as the eye, to compensate for removed fluid and tissue. This prevents the eye from collapsing. In addition, the irrigation fluid can be used to wash away or to position tissue within the operating field by suitably rotating the instrument. It also serves as a transporting means forming a suspension with the separated material.

A reverse flow fluid can be supplied through the conduit 24 into the central passage 58. It is sometimes desired to use this fluid to move particles which may have been trapped in the central passage 58 or in the drill flutes 37b. One type of fluid control system for the suction, irrigation and reverse fluid flows is described in my copending application Ser. No. 208,282, filed Dec. 15, 1971 now U.S. Pat. No. 3,812,855 dated May 28, 1974 entitled "System for Controlling Fluid and Suction Pressure" which is assigned to the same assignee.

FIGS. 7 and 8 show another embodiment with a cutting action at the front of the probe instead of at the side as in FIGS. 1–6. Here the nose cone 76 has an opening 87 with a lower cutting edge 88 in its front wall 89. As seen in FIG. 8, opening 87 may be round, of a tear drop shape, or any other suitable configuration. The wall 89 is substantially flat and is angled downwardly so that it projects slightly forward along a line through the irrigation fluid opening 60.

The front edge 37d of the cutter 37 is sharpened and it is urged against the inner surface of the front wall 89 by the spring 76. The cutter rotates in a direction toward the narrower portion of opening 87. As in the case of FIGS. 1–6, the evacuation flow in passage 58 draws the tissue into the opening 87 where it is cut off by the shearing action between the blades 37d and the opening wall 88. The use of the irrigation fluid and reverse flow fluid is as previously described.

FIG. 9 shows one arrangement for mounting the optic material. The outer shell 56 is split longitudinally along a portion of the length thereof and bent inwardly to leave a gap. The bent ends 56a of shell 56 are suitably bonded, such as by welding, soldering or other similar process to the outer surface of the inner shell 54 to preserve the fluid-tight integrity of the outer passage 59. A fiber optic rod, or bundle of fibers 92 is located in the gap between the bent-in ends of the shell 56 and are held in place by a suitable adhesive such as an epoxy 94. The optical member 92 extends substantially along the entire length of probe 10, as shown in FIG. 1. The member 92 extends slightly above the outer circumference of shell 56. Member 92 can be used either for viewing the operating field or for applying light thereto.

FIG. 10 shows a further embodiment for mounting the optical member 92. Here the gap between the bent-in ends 56a of the outer shell 56 is made larger and deeper. The optical member 92 is now totally within the gap. The length of legs 56a bring the lower surface of the inner shell 54 closer to the outer shell 56. Since this restricts the cross-sectional area of the irrigation fluid passage where opening 60 would normally be, two openings 60a are formed in shell 56, one on each side of the central longitudinal plane of the probe. The epoxy 94 used to hold optical member 92 rounds off the outer shell.

FIGS. 11 and 12 show a still further embodiment of the invention in which the outer shield 56b is provided with two pairs of bent legs 56c and 56d to provide two gaps into which respective optical members 92a and 92b are laid and held by the adhesive 94. One of the optical members 92 can be used for illumination and the other for viewing. As shown in FIG. 11, openings 60c are provided for the irrigation fluid on each solid portion of the outer shell 56b. Only one opening 60 can be used for the irrigation fluid as shown in FIG. 12.

In each of the embodiments of FIGS. 11 and 12, one of the optical members 92 can be used for illumination of the operating field and the other for viewing. Any suitable arrangement of lamps, high intensity light sources, eye-pieces, etc., can be used for this. Where only a single optical member 92 is used, such as in FIGS. 9 and 10, it can be split into two parts, one used for illumination and the other for viewing. This can be accomplished with a bundle of optical fibers.

FIG. 13 shows another embodiment of the invention in which an optical member 92, such as shown in FIGS. 9–12, is also utilized. As seen, the end of the optical member 92 terminates in an angled front face 93 so that the light, or the viewing area is over the opening 64. Thus, the operator of the instrument can illuminate and/or view, the tissue being drawn against the cutter. This particular configuration can be used with an optical member of any of the embodiment of FIGS. 9–12.

In FIG. 13, an electrode 98 located within an insulating sleeve 99 is located on the probe 10. While the electrode 98 is shown spaced from optical member 92 by about 180°, any desired spacing can be used. Both the optical member 92 and the electrode 98 can be mounted to the probe in the manner shown in any of FIGS. 9–12.

The front end 100 of the electrode extends beyond the insulating sleeve 99. Electrical connections (not shown) are brought out from the electrode 98 to a suitable source of current. The electrode can be used for diathermy, cauterization or other purpose in accordance with the type of current and energy supplied to it.

As an alternative, the electrode 98 can be replaced by a hollow tubular member capable of conveying a cold gas. This enables the instrument to be used for cryosurgery. In either the case of an electrode or a tube, the instrument permits the functions that these auxiliary elements can perform to be carried out in a small space, such as the eye, in combination with the main cutting action of the instrument. This eliminates the need for a surgeon to remove and replace various instruments, capable of performing only one function, out of and into the operating field. This increases the effectiveness of the operation.

The use of the fluted cutter 37 provides a further advantage in that the rotation of the cutter flutes produces a force component backwards, toward the cup 12. This aids in sweeping the cut particles away from opening 64 back toward the bore 68 and out of the instrument.

What is claimed is:

1. A surgical instrument for cutting tissue comprising a first tubular member having a closed end portion, said first tubular member formed with an opening therein for the tissue to enter to be cut, said first tubular member also formed with a shearing surface around at least a portion of the opening, a cutting tool within said tubular member, said cutting tool including an elastic shaft having a cutter at one end and said cutter having a body with a fluted cutting surface formed thereon which extends around the outer surface of the body and along the axis thereof, means engaging said shaft for rotating said cutting tool, resilient means for acting on the elastic shaft of said cutting tool in a direction longitudinal of the shaft urging the cutter toward the closed end portion of the first tubular member and the fluted cutting surface of the cutter into positive engagement with the inner surface of said first tubular member in the area of said shearing surface, said cutter cutting surface and said opening shearing surface providing a shearing action on the tissue in said opening as the cutter cutting surface sweeps across the opening.

2. An instrument as in claim 1 further comprising means for applying a force to the interior of said first tubular member for drawing material into said opening to be cut.

3. An instrument as in claim 1 wherein said means for rotating the tool comprises a motor.

4. An instrument as in claim 1 wherein the inner surface of the portion of the first tubular member engaged by the fluted cutting surface has a generally conical portion with an included angle of substantially about 11° with respect to the longitudinal axis of said first tubular member.

5. An instrument as in claim 1 wherein said opening is located on a side of said closed end of said first tubular member.

6. An instrument as in claim 5 wherein said opening is generally circular.

7. A surgical instrument as in claim 1 wherein said tubular member has an end portion with said opening being at the front thereof, said cutter body formed with a cutting surface at the front end thereof which engages the shearing surface of said opening.

8. An instrument as in claim 7 wherein said opening is of a generally tear drop shape.

9. An instrument as in claim 7 wherein the outer surface of said cutter is generally cyclindrical and said fluted cutting surface is helical.

10. An instrument as in claim 1 further comprising elongated optical means mounted adjacent at least a portion of said first tubular member.

11. An instrument as in claim 1 further comprising a second tubular member of larger diameter than said first member mounted over at least a portion of said first tubular member and defining a fluid flow passage therebetween, said second tubular member formed with an opening in the wall thereof.

12. An instrument as in claim 11 wherein said second tubular member is slit along at least a portion of the length thereof, the ends of said second member formed by the slit being bent and attached to the outer surface of the first tubular member, leaving a gap between said ends, and an elongated auxiliary member located in said gap.

13. An instrument as in claim 12 wherein two slits are formed in said second tubular member whose ends are attached to said first tubular member to form a pair of gaps, and an elongated auxiliary member in each of said gaps.

14. An instrument as in claim 13 wherein said second tubular member is formed with an opening in each portion thereof communicating with the passage between said first and second tubular members.

15. An instrument as in claim 1 wherein the fluted cutting surface of the cutter makes contact with the shearing surface of the opening at two points as it sweeps across the opening and said cutter cutting surface extends into said opening.

16. An instrument as in claim 13 wherein said fluted cutting surface extends for at least one full turn around the body of the cutter to provide at least one additional point of support for the cutter surface spaced from said opening by the engagement of at least one additional point of said fluted cutting surface with a point on the interior of said first tubular member.

17. An instrument as in claim 1 wherein the end portion of said first tubular member is a truncated generally conical shaped nose piece in which said opening is formed, and stop means on the interior of said end portion and engaging said cutter for spacing the front end of the cutter from the front end of said nose piece.

18. An instrument as in claim 1 wherein the diameter of the fluted cutting surface of the cutter where it sweeps across said opening is greater than the internal diameter of the corresponding part of the tubular member.

19. An instrument as in claim 1 wherein said cutter body has a free end, and means on the interior of said first tubular member and spaced from the closed end of the first tubular member for providing a stop for the body at its free end.

20. A surgical instrument as in claim 1 wherein said opening is formed in the side of the first tubular member, said cutter body having a free end and a tapering shape of increasing cross-section from the free end toward the rear of said body, said first tubular member having an end portion of tapering shape corresponding to the cutter body.

* * * * *